US 6,599,271 B1

(12) United States Patent
Easley

(10) Patent No.: US 6,599,271 B1
(45) Date of Patent: Jul. 29, 2003

(54) OPHTHALMIC FLOW CONVERTER

(75) Inventor: James C. Easley, St. Charles, MO (US)

(73) Assignee: Syntec, Inc., Winfield, MO (US)

( * ) Notice: Subject to any disclaimer, the term of this patent is extended or adjusted under 35 U.S.C. 154(b) by 0 days.

(21) Appl. No.: 09/549,145

(22) Filed: Apr. 13, 2000

Related U.S. Application Data

(60) Provisional application No. 60/129,062, filed on Apr. 13, 1999.

(51) Int. Cl.[7] .................................................. A61M 1/00
(52) U.S. Cl. ........................ 604/119; 604/30; 604/320; 604/323; 604/521; 604/902; 606/107; 606/166; 601/13
(58) Field of Search ................................. 604/319–326, 604/902, 521, 294, 119, 30; 606/166, 107; 601/13

(56) References Cited

U.S. PATENT DOCUMENTS

| | | | |
|---|---|---|---|
| 3,693,613 A | | 9/1972 | Kelman |
| 3,902,495 A | | 9/1975 | Weiss et al. |
| 4,772,256 A | * | 9/1988 | Lane et al. ..................... 604/4 |
| 5,106,367 A | | 4/1992 | Ureche et al. |
| 5,141,504 A | * | 8/1992 | Herweck et al. ............ 604/317 |
| 5,195,960 A | * | 3/1993 | Hossain et al. ............... 604/34 |
| 5,569,188 A | | 10/1996 | Mackool |
| 5,643,200 A | * | 7/1997 | Edwards ....................... 604/27 |
| 5,704,927 A | | 1/1998 | Gillette et al. |
| 5,725,495 A | | 3/1998 | Strukel et al. |
| 5,733,256 A | | 3/1998 | Costin |
| 5,741,237 A | * | 4/1998 | Walker ........................ 604/317 |
| 5,766,146 A | | 6/1998 | Barwick, Jr. |
| 5,772,644 A | * | 6/1998 | Bark et al. ................... 604/317 |
| 5,785,700 A | * | 7/1998 | Olson .......................... 604/408 |
| 5,810,765 A | | 9/1998 | Oda |
| 6,312,440 B1 | * | 11/2001 | Hood et al. .................. 606/166 |
| 6,406,454 B1 | * | 6/2002 | Hajianpour .................... 604/48 |
| 6,506,176 B1 | * | 1/2003 | Mittelstein et al. ........... 604/22 |

FOREIGN PATENT DOCUMENTS

EP 0862902 9/1998

* cited by examiner

*Primary Examiner*—Weilun Lo
*Assistant Examiner*—Michael Bogart
(74) *Attorney, Agent, or Firm*—Polster, Leider, Woodruff & Luchesi, L.C.

(57) ABSTRACT

A device for preventing post occlusion flow surges during eye surgery includes an enclosure defining an inlet and an outlet. The enclosure further defines a flow passage between the inlet and the outlet. A restriction is positioned in the flow passage. Structure preferring a filtering function is placed upstream of the restriction for permitting fluid passage through the device. The enclosure further defines a storage area for collecting material restrained by the filter structure. In the preferred embodiment, the device is constructing from a suitable plastic or other molded material, and is intended for disposable use.

21 Claims, 6 Drawing Sheets

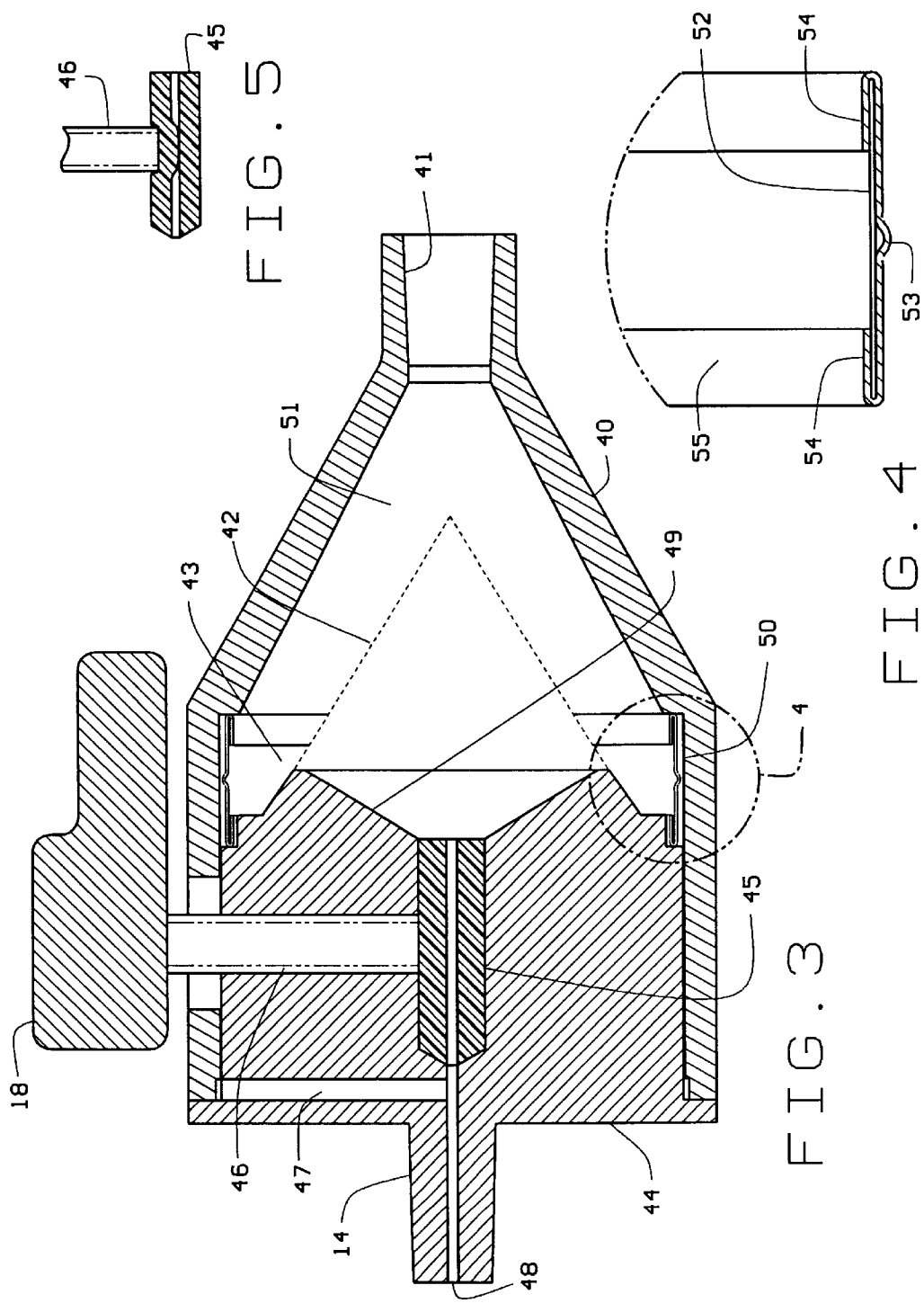

OPHTHALMIC FLOW CONVERTER

CROSS-REFERENCE TO RELATED APPLICATIONS

This application claims the benefit of a provisional Application No. 60/129,062 filed Apr. 13, 1999.

STATEMENT REGARDING FEDERALLY SPONSORED RESEARCH OR DEVELOPMENT

Not Applicable.

BACKGROUND OF THE INVENTION

This invention relates to eye surgery machines and in particular, for surgery machine finding application in ophthalmic operations. While the invention is described with particular emphasis in the use of the invention in cataract surgery, those skilled in the art will recognize the wider applicability of the inventive principles discussed hereinafter.

A cataract is the lens of the eye after it has become cloudy. Surgery to remove cataracts has been preformed for many years. Current practice is to remove the cataract by phacoemulsification, replacing the lens with an artificial one. Phacoemulsification utilizes a tube, usually referred to as an ultrasonic needle that is vibrated at ultrasonic frequencies to break up or emulsify the cataract. The needle is driven by a multi-function ultrasound handpiece. The handpiece conventionally includes an ultrasonic motor and fluid channels for aspiration and irrigation of the eye. Aspiration is used to evacuate the lens and other vitreous material from the eye. Irrigation replaces the volume removed by aspiration.

It is vitally important to maintain the intraocular pressure at an appropriate level during ophthalmic operations, by controlling the irrigation and aspiration capacity, thus preventing, in particular, the cornea from collapsing. Corneal collapse occurs when the system fails to supply sufficient inflow to the eye that compensates for the aspirated amount of liquid and/or tissue being removed, so that the device creates a vacuum within the eye itself.

In the past, a bag or bottle is normally used to store irrigation fluid. The fluid is connected to the ultrasound handpiece through flexible surgical tubing. The fluid is delivered to the handpiece under pressure, relative to the surrounding atmosphere. The pressure is developed either by gravity, i.e., hanging the bottle at an elevation greater than the handpiece, by pressurizing the bottle with air, or by using a pumping mechanism, for example. Ultrasound handpieces conventionally have a coaxial fluid flow design along the instrument tip. An irrigation sleeve surrounds the ultrasound needle. The sleeve is normally constructed from a pliable material, for example, silicone and rubber, which is intended to conform somewhat to the shape of the incision in the eye, thereby reducing wound leakage. A connection is made at the handpiece, between the irrigation sleeve and the tubing from the bottle. Fluid enters the eye through ports near the end of the sleeve.

Fluid and tissue are aspirated from the eye through a channel located inside the ultrasound needle. The channel through the ultrasound needle is in fluid communication with a connection on the back of the handpiece. Conventionally, flexible surgical tubing is connected to the handpiece at one end and to the surgery machine at the other end. Vacuum for aspiration is supplied to the tubing by the surgery machine. Surgery machines use various methods for controlling the vacuum level provided for aspiration. They also use various methods for storing the spent fluid and tissue.

During an eye operation, ideally pressure within the eye is maintained at a constant level regardless of fluid flow changes or wound leakage. In practice, pressure can vary a great deal, depending on fluid flow dynamics. One cause for pressure changes is the position of the eye in the fluid flow path. Conventionally, fluid flow restrictions exist between the fluid source, i.e., the irrigation bottle, and the eye. Fluid flow restrictions also exist between the eye and the vacuum or aspiration source. These restrictions cause a pressure drop, which is proportional to fluid flow, as fluid flows from the fluid source through the eye and to the vacuum source. As will be appreciated by those skilled in the art, as fluid flow increases, the pressure inside the eye decreases, it being assumed the fluid pressure at the bottle is a constant.

An additional cause for pressure change is the elastic nature of the tubing connecting the eye to the vacuum source. The diameter of the tubing changes, based on the pressure difference between the inside of the tubing and atmospheric pressure. That is to say, the tubing becomes smaller as vacuum increases. These diameter changes cause the tubing to store energy, damping pressure changes in the tubing. Often during surgery, the tip of the ultrasound needle becomes occluded. With occlusion, the pressure in the anterior chamber of the eye equalizes to the pressure of the fluid source and the pressure inside the ultrasonic needle approaches that of the vacuum source. When the occlusion breaks suddenly, the energy stored in the aspirating tubing causes a surge of fluid to flow, as the tubing returns to the size it was before the occlusion. The flow surge causes the pressure in the anterior chamber of the eye to decrease to a point lower than it would be under constant flow conditions. While this pressure change is momentary, it can be great enough to cause the pressure in the anterior chamber to be less than atmospheric pressure, causing the chamber to collapse.

In addition, any air in the aspiration tubing can exacerbate the pressure problem during surgery. Air bubbles can form from cavitation caused by the ultrasound needle, or from inadequate purging of the aspiration tubing during set up. Because of the compressible nature of air, the bubbles expand under vacuum, then contract as the vacuum is reduced.

Procedurally, fluid flow through the anterior chamber of the eye is used to manipulate tissue within the anterior chamber. As fluid moves, it tends to push items, for example lens material, membranes, and other undesirable debris, towards the tip of the ultrasound needle. To an observer, it appears as if the tip of the needle attracts material toward it. At very low flow rates, the attraction is small, and only things that are close to the tip move towards it. As the fluid flow rate increases, the apparent attraction is greater. At high flow rates, anything in the anterior chamber that is free to move is attracted to the tip of the ultrasound needle. The surgeon takes advantage of this tendency, because the tendency allows the ultrasound tip of the handpiece to remain near the middle of the anterior chamber most of the time, yet provides access to the tissues necessary to accomplish the surgery. The middle of the anterior chamber of the eye generally is considered a safer place to operate, reducing the likelihood of complications from the surgery.

In counter distinction to the attraction discussed above, as ultrasound energy, used to emulsify the lens, is increased, the needle tip tends to push the material intended for emulsification away from the needle tip. This push is greater with higher amounts of ultrasonic energy. However, a higher or greater amount of ultrasound energy is required to emulsify denser harder lenses than is required to emulsify softer lenses. In order to allow efficient transfer of energy to the lens, the lens must be kept against the needle tip. However, when the lens is positioned against the tip of the ultrasound needle, the lens tends to occlude the tip. The pressure difference develops across the lens, forming a holding force against the needle tip. The vacuum level at its source, the irrigation pressure, and the ultrasound needle inside diameter determines the maximum amount of force available to hold the lens. Aspiration assisted phacoemulsification occurs when the holding force generated by the fluid is much greater than that necessary to overcome the opposite push of the ultrasonic source. High vacuum causes stress in the lens to be higher, reducing or eliminating the need for higher ultrasound power to emulsify the lens. I am aware of medical studies that have shown a correlation between total ultrasound power used in phacoemulsification, and cornea endothelial cell loss. Because endothelial cells are not replaced by the body, the loss of the cells can be a serious surgical complication.

In general, the source of vacuum for aspiration when used for phacoemulsification can be provided in various forms. One form is a peristaltic pump, the operation of which causes the pump to act as a constant flow pump. That is to say, a vacuum developed by the pump increases with resistance to flow. An alternative source for vacuum for aspiration is a constant vacuum source. An example of a constant vacuum source is a venturi pump. A venturi pump is virtually insensitive to changes in flow resistance. There are then, generally speaking, two broad classes of surgery machines, one is the constant vacuum source and other is the constant flow source. Regardless of the type, however, phacoemulsification procedures performed with either machine work on the attraction/repulsion operation of the fluid and ultrasonic power described above.

Adjusting the different function valves of the surgery machine for ophthalmic procedures is a balancing act involving many factors influencing the adjustment. Maintenance of the pressure in the anterior chamber of the eye is the controlling factor. However, the maximum pressure allowed in the anterior chamber determines the maximum pressure setting for irrigation and the maximum flow rate available for irrigation. The aspiration flow setting is determined by the desired amount of attraction to the ultrasound needle. The density of the lens, coupled with a desire to complete surgery in the shortest possible time, affect the desired amount of ultrasonic power. The amount of ultrasonic power utilized, coupled with the inside diameter of the ultrasound needle determine the desired maximum vacuum setting. A change in any of the component characteristics used in the procedure can result in changing the usable ranges of all of the function adjustments.

As phacoemulsification surgery has increased in popularity, a number of solutions intended to control the pressure in the anterior chamber of the eye during surgery have been proposed. For example, the U.S. Pat. No. 5,766,146, describes a method of controlling the irrigation flow rate by using multiple irrigation sources. U.S. Pat. No. 5,810,765, also describes a method of controlling the irrigation flow rate by either changing the irrigation bottle pressure or connecting multiple irrigation bottles which differ in height, to the eye. U.S. Pat. No. 3,902,495, describes a device which vents automatically to reduce the vacuum in the aspiration tubing if the vacuum exceeds a preset limit. U.S. Pat. No. 4,935,005 ('005), describes a surgeon controlled connection of the aspiration tubing and the irrigation tubing to enable the surgeon to release access vacuum and equalize the pressure. The '005 patent also describes a structure for blocking the aspiration tubing when a preset vacuum limit is exceeded. U.S. Pat. No. 3,693,613, describes using a vent to reduce vacuum automatically in the aspiration tubing if a sudden increase of flow in the aspiration tubing is sensed by the surgery machine. U.S. Pat. No. 4,494,342, describes connecting the irrigation tubing to the aspiration tubing automatically if a sudden increase in flow is sensed in the aspiration tubing. U.S. Pat. No. 5,569,188, proposes temporarily reversing the peristaltic pump, while U.S. Pat. No. 5,649,904, describes using a reflex mechanism in the aspiration tubing to reduce flow surge. U.S. Pat. No. 5,733,256, uses sensors near the ultrasound handpiece to reduce reaction time to changes in flow or pressure. U.S. Pat. No. 5,160,367, describes using a section of elastic tubing in the aspiration flow line, which has the effect of damping the post occlusion flow surge. U.S. Pat. No. 5,476,448, describes a device attached to the aspiration tubing that includes an elastic dome that collapses under increase vacuum, blocking the aspiration tube. The elastic dome returns to normal after the occlusion is cleared. U.S. Pat. No. 5,725,495, discloses a valve that squeezes the aspiration tubing to occlude aspiration flow rate. The valve is automatically controlled by the surgery machine. European Patent Application. No. 0 862902 describes a dome shaped plastic membrane which is connected into the irrigation line. The membrane forms a reservoir and dampens irrigation pressure changes. This wide body of art proposing solutions to the problems with eye surgery machines used in actual practice demonstrates that there is still a need for a device to prevent post occlusion flow surges during eye surgery.

BRIEF SUMMARY OF THE INVENTION

It is therefore, one of the objects of this invention to provide a device by which high maximum aspiration vacuum level may be obtained without experiencing significant post occlusion flow surges during eye surgery.

It is another object of this invention is to provide a device that allows the use of higher maximum aspiration vacuum levels in combination with normal or large bore ultrasonic needles without experiencing significant post occlusion flow surges during eye surgery.

It is another object of this invention to provide a device to prevent post occlusion flow surges during eye surgery which is tolerant to air bubbles in the aspiration tubing.

Another object of this invention is to provide a device for reducing the amount of ultrasound energy necessary to dissassemble a cataract by use of high vacuum aspiration without experiencing a significant post occlusion flow surge during eye surgery.

Yet another object of this invention is to provide a device which allows a constant vacuum source to be used for aspiration during phacoemulsification surgery without performance compromises when compared to a constant flow vacuum source.

Another object of this invention to provide a device which maybe employed effectively with both constant vacuum and constant flow surgery machines and instruments that are currently in use.

Another object of this invention is to provide a relatively low cost, device for preventing post occlusion flow surges.

Yet another object of this invention to provide a disposable device for prevent post occlusion flow surges during eye surgery.

Other objects of this invention will be apparent to those skilled in the art in light of the following description and accompanying drawings.

In accordance with this invention, generally stated, a device is inserted along the aspirating line of an eye surgery machine. The machine includes a handpiece for performing eye surgery. Preferably the device of the present invention is attached in the aspirating line at the handpiece. The device includes an enclosure having an inlet and an outlet. A flow passage extends between the inlet and the outlet. In the preferred embodiment, the inlet of the device is attached to the handpiece and the outlet of the device is attached to the vacuum line of the surgery machine. The device includes a restriction in the flow path of the device, which defines a flow limit for aspirated fluids. A filter is positioned in the flow path upstream of the restriction. The device enclosure has a predetermined storage capacity for retaining material blocked by the filter. The preferred embodiment further includes a second passage in the enclosure between the filter and a point downstream of the restriction for permitting passage of air bubbles, for example, which sometimes enter the aspirating stream during surgery.

BRIEF DESCRIPTION OF THE SEVERAL VIEWS OF THE DRAWINGS

In the drawings.

FIG. 3 is a sectional view taken along the line 3—3 of FIG. 2;

FIG. 4 is an enlarged view taken about the area 4—4 in FIG. 3;

FIG. 5 is a diagrammatic view illustrating an adjustable feature for the device shown in FIG. 3;

Corresponding reference numerals will be used throughout the several figures of the drawings, where appropriate.

DETAILED DESCRIPTION OF THE INVENTION

Figure 1:
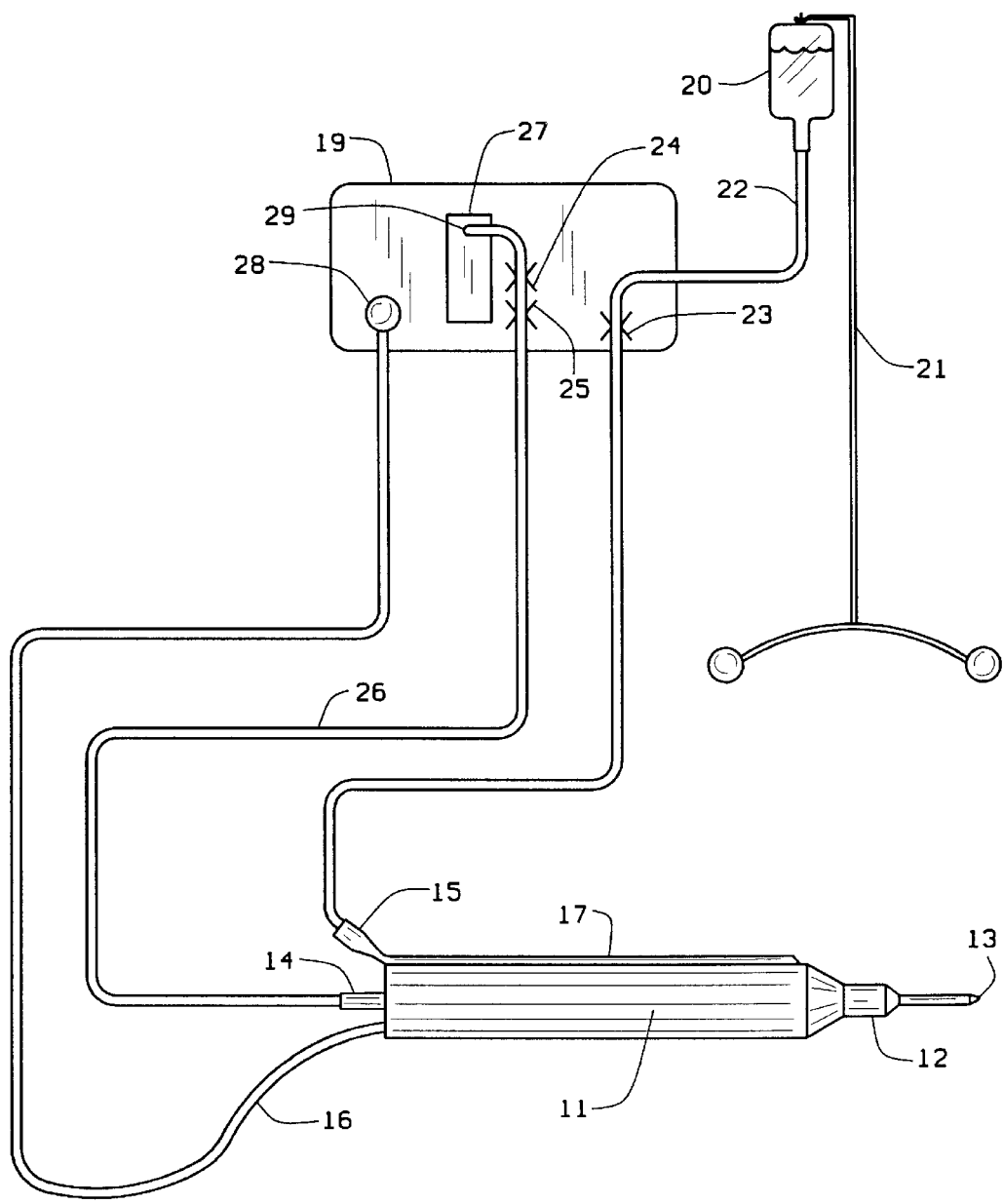
FIG. 1 is a diagrammatic view of a prior art eye surgery machine.

Referring now to FIG. 1, a prior art constant vacuum surgery machine 19 for phacoemulsification includes an ultrasound handpiece 11. The ultrasound handpiece 11 has an aspiration conduit 12 formed in it, the conduit 12 having an ultrasound needle 13 attached to its distal end. A sleeve 17 for irrigation fluid is attached to the conduit 12 and is carried along the exterior surface of the ultrasound handpiece 11. A connector 15 is provided at the handpiece 11 for permitting attachment of an irrigation tube 22 to the handpiece. A second end of irrigation tube 22 is connected to an irrigation bottle 20. Irrigation flow commonly is controlled by a pinch valve 23 on the surgery machine 19.

Conventionally, an aspiration tube 26 is connected to an aspiration connection 14 on a first end, and to an aspiration connection 29 of an aspiration cassette 27 associated with the surgery machine 19. The aspiration cassette is normally provided on constant vacuum surgery machines for waste storage, and to communicate vacuum to the handpiece 11 from a vacuum source associated with the machine 19, the vacuum source not being shown in the drawings, via an aspiration connection 29 of the machine 19. A pair of pinch valves 24 and 25 control the flow in aspiration tubing 26 and, as indicated, provide a reflux function. A cable 16 provides power and control to the ultrasound handpiece 11, which is connected to the surgery machine 19 at an output terminal 28 of the machine.

Figure 2:
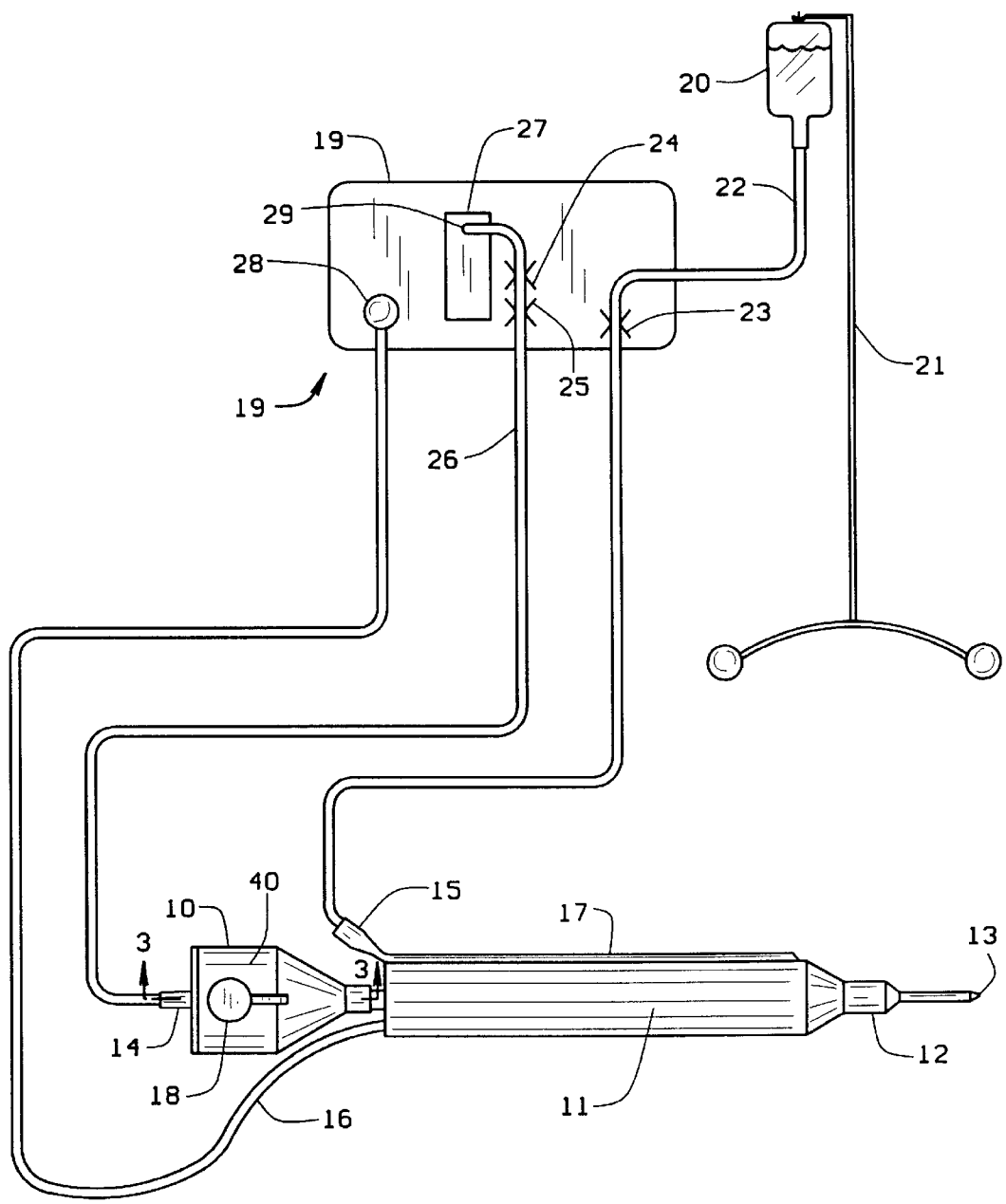
FIG. 2 is a diagrammatic view of one illustrative embodiment of a surgery machine employing a first illustrative embodiment of surge suppression device of the present invention.

I have found that the conventional apparatus shown in FIG. 1 can be enhanced by the use of a control device 10, a first embodiment, which is shown in FIG. 2. The control device 10 preferably is connected to the aspiration outlet of the handpiece 11, and the aspiration connection 14 is connected to the device 10 instead of the handpiece 11. In other respects, operation of the machine 19 shown in FIG. 2 is similar to the prior art device shown in FIG. 1.

Referring now to FIGS. 2 and 3, the device 10 includes an enclosure or outer shell 40. An adjustment control 18 is available to the surgeon exteriorly of the enclosure 40. The device 10 includes a connection 41 for attaching device 10 to the ultrasound handpiece 11. A manifold 44 is positioned within the enclosure, and has a fluid channel 48 extending through it. The manifold 44 also defines, with the enclosure 40, an air passage 47. The air passage 47 is connected to an air path 50. In this embodiment, the manifold 44 also includes an inverted conically shaped feed end 49. A conically shaped hydrophilic filter 42 is attached to the manifold 44 and provides filtration of lens particles and tissues. The filter 42 is mounted within a volume 51 defined by the enclosure 40. A second hydrophobic filter 43 is mounted along the manifold 44 and is arranged to permit the passage of air bubbles from the volume 51 to the channel 48 through the air passage 50 and 47, as later described in greater detail. A variable orifice 45 is provided within the manifold 44 as a portion of the channel 48.

An adjustment structure 46 also is mounted along the manifold 44 and is operatively connected to the control 18. As shown in FIG. 5, the variable orifice 45 is deformable by operation of the adjustment 46 to control the size of the channel 48, thereby controlling the amount of vacuum applied to the handpiece 11.

The filter 42, as indicated above, is, in the embodiment illustrated, conical in shape and is attached to the manifold 44 by any convenient method. Coining, staking or suitable adhesive may be used, for example. Mounted externally of the filter 42 is a filter 43. Filter 43 is annular in design and includes an outer holder 55 for containing a hydrophobic membrane for the filter 43. Filter 43 includes a hydrophobic membrane 52 preferably constructed from a Teflon based material that exhibits hydrophobic characteristics. Other materials are compatible with the broader aspects of this invention. The holder 55 preferably is constructed from stainless steel or other appropriate material, and is formed to trap the membrane 52 under an edge 54 for supporting the membrane 52 in place. The holder 55 also has a groove 53 formed in it. The groove 53 prevents the filter 43 from sealing against the enclosure 40, and defines the air passage or gap 50 with the enclosure 40. The frame 55 has a plurality of openings formed in it, not shown, which permits air which passages through the membrane 52 to pass through the frame 55 and into the gap 50 for communication to the passage 47, as described above. That is to say, air that air passes through the hydrophobic filter 43 is in fluid communication with the aspiration output connector 14 of the machine 19 through the interstitial space between the enclosure 40 and the manifold 44 through the openings 47 and channel 48.

Hydrophilic filter 42, preferably is constructed from a fine mesh material such as polyester cloth. In the preferred embodiment, the cloth has a mesh opening between 20 and 200 microns. Other materials and mesh openings may be employed, if desired.

The orifice 45 preferably is molded in place using a silicone rubber compound. Again, as will be appreciated by those skilled in the art, other materials may be employed if desired. The adjustment device 45 also preferably is constructed from plastic or other corrosion resistant metal, and the manifold may have suitable threads formed in it, not shown, to permit movement of the adjustment device 46 in a conventional manner. As shown and described with respect to FIG. 5, movement of the control 18 moves adjustment 46 upwardly or downwardly with respect to FIG. 3, varying the opening of the orifice 45.

As indicated, FIG. 5 shows the orifice 45 in a nearly closed position, which is representative of the adjustment when the control device 10 is being used. The diameter of the opening through the channel 48 affects the range of flow adjustment for the device 10. The diameter of the channel may be modified to make the device more appropriate for a specific use, but I have found that in general the diameter may be less than 0.060 inches for phacoemulsification surgery. The pitch of the threads associated with the adjustment 18 also effects the sensitivity of flow adjustment through the channel 48. The sensitivity can be modified, but preferably requires less than one full turn for minimum to maximum flow to avoid confusing the user about the flow device adjustment. When the machine 19 is set up for surgery, the device 10 is connected to the ultrasound handpiece 11 with the flow adjustment set to maximum. Tubing connections are made and instruments are assembled in a normal manner. Adjustments to the aspiration function of the surgery machine 19 normally are made at this time. Constant flow machines are adjusted to a flow rate higher than that expected to be used during surgery, since the device 10 will be used to control the actual flow rate. Both constant flow and constant vacuum machines maximum vacuum setting are adjusted to the desired maximum amount to be attained during surgery.

The distal end of the ultrasound handpiece 11 then is submerged in irrigation solution. A prime cycle is preformed i.e., aspiration is delivered for a time period with a handpiece held vertically. This orientation allows the device 10 to purge all internal air quickly. As fluid begins to flow through connection 41. Air is evacuated through both filters 42 and 43. Fluid will begin to fill volume 51 until it wets filter 42. As indicated above, the manifold 44 preferably has an inverted conical shape 49 directing air towards the opening of the variable orifice 45 until fluid fills the entire volume of filter 42. Any air trapped in volume 51 after filter 52 has become fully wetted will clear the device through filter 43. As will be appreciated by those skilled in the art, after filter 42 becomes wetted with irrigation fluid, it will tend not to pass air, because there will normally not be a great enough pressure difference across filter 42 to break the surface tension of the fluid. Without an alternative route for air passage through the device, air bubbles would tend to be trapped causing a significant increase in post occlusion flow surge. However, my design permits passage of air through the filter 43, regardless of the operating condition of the filter 42. After air has been purged from the device, the desired flow rate, giving the appropriate amount of attraction for the intended surgery, may be obtained using the adjustment 18.

As surgery progresses, the pressures in the fluid flow system of the present invention are different from those encountered with prior art methods. The aspiration tubing, like the irrigation tubing, preferably is designed to offer the lowest restriction practical. This causes the aspiration tubing to have a lower pressure drop with flow, reducing negative interaction of the aspiration tubing with the operation of the rest of the fluid flow system. With aspiration tubing that has a low flow restriction, the pressure at connector 14 is nearly the same throughout the expected fluid flow range. When fluid flow is at the maximum rate (i.e., ultrasound needle not occluded) most of the pressure is dropped across the variable orifice 45 in the device 10, with a portion of the pressure drop occurring across the ultrasound needle. When the ultrasound needle becomes partially occluded, increasing the flow restriction of the ultrasound needle, the vacuum level at the tip of the ultrasound needle will begin to increase. The vacuum level of the fluid path between the variable orifice 45 and the tip of the ultrasound need will also increase, however the volume of the space between the variable orifice and the ultrasound needle changes an insignificant amount. When the ultrasound needle becomes fully occluded, the vacuum level at the tip of the ultrasound needle goes to the vacuum level attained at the surgery machine 19. The pressure drop across the variable orifice 45 decreases to 0. Again, the volume of the space between the variable orifice and the ultrasound needle tip changes an insignificant amount. When the occlusion breaks, the flow rate through the system returns immediately, without a significant flow surge, to a value very near the flow rate with the ultrasound needle not occluded. I found this is due to the lack of volume change between the variable orifice and the ultrasound needle tip with vacuum changes. The preferred embodiment of my invention accomplishes this result with a relatively low cost, easy to manufacture design.

As can be seen, the inside diameter of the ultrasound needle does not effect post occlusion flow surge when used with the device 10. The embodiment of FIG. 2 can be adjusted to compensate for the different flow restrictions posed by using ultrasound needles with different bore sizes. As will be appreciated by those skilled in the art, this allows the ultrasound needle's inside diameter to be larger, providing improved holding power. In turn, improved holding power allows higher ultrasound power use. It also can be seen that increasing the aspiration vacuum level has no significant effect on post occlusion flow surges. This allows the use of higher aspiration vacuum levels required for aspiration assisted phacoemulsification. The device provides a means for quickly causes air to be passed to the aspiration tubing. Volume changes experienced by the air in the aspiration tubing using my device has an insignificant effect on operation of the surgical machine 19. It is also apparent that the device can operate equally well from either constant flow or constant vacuum surgery machines. Either type of machine is operated in a way as to operate as a constant vacuum source. The fluid flow system operates as a constant flow source.

Figure 6:
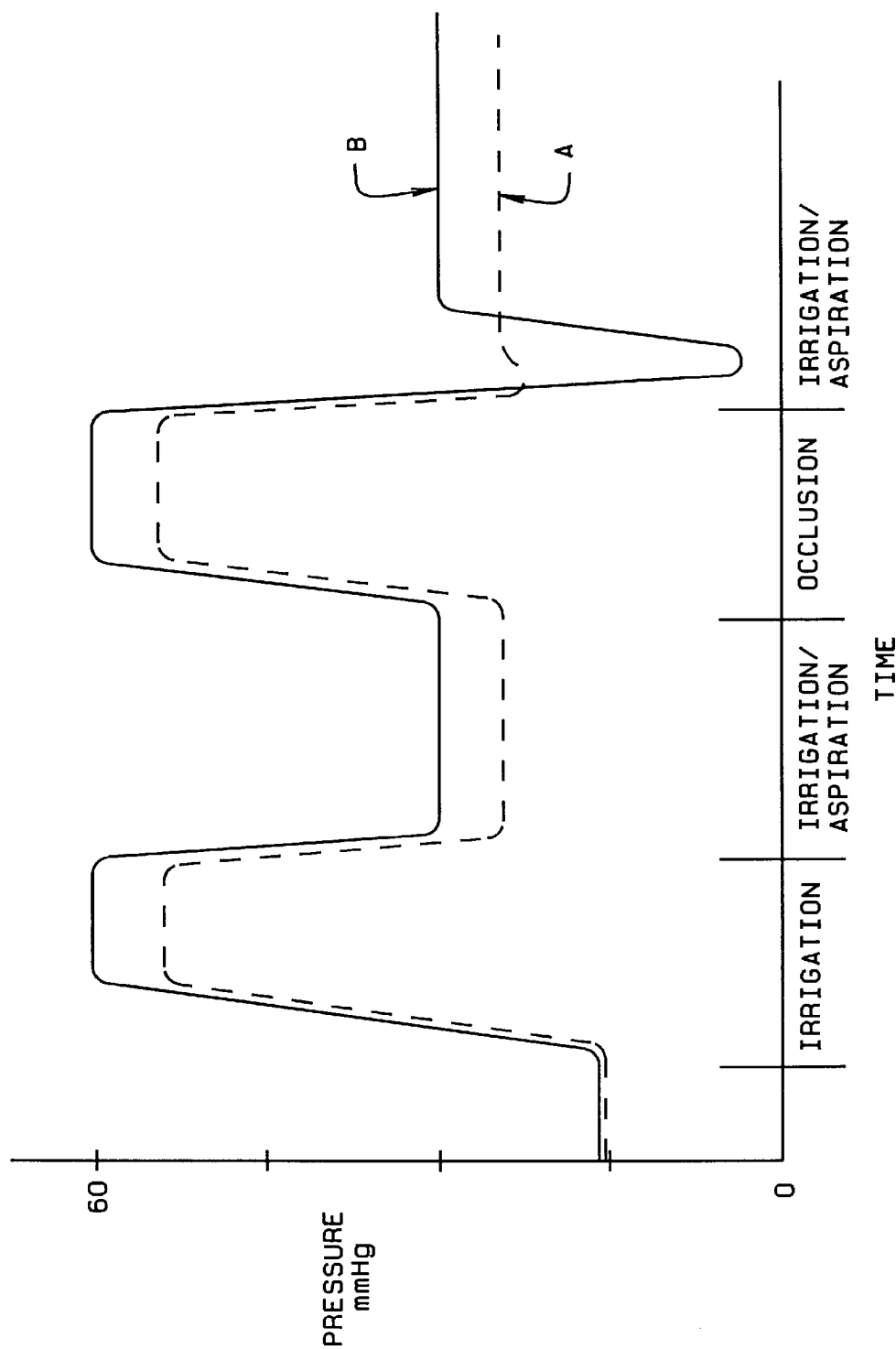
FIG. 6 is a diagrammatic view illustrating the performance improvement obtainable with the device of the present invention.

The improvement obtainable with the device of the present invention is graphically illustrated in FIG. 6. Anterior chamber pressures obtained during use of prior art surgical methods are illustrated by the solid line curve B, and the operation of the surgical machine 19 employing the device 10 is illustrated by the dash line curve A. Those skilled in the art will recognize that both devices experience significant pressure differences when irrigation alone is being provided, and when aspiration is on with irrigation. The most dramatic difference in operation occurs during the period immediately after an occlusion is released. With prior art systems, a significant post occlusion flow surge occurs.

The maximum aspiration vacuum attained with prior art systems has to be limited, or the post occlusion flow surge is great enough to cause the anterior chamber of the eye to collapse. In contrast, curve A exhibits virtually no post occlusion flow surge. This allows the maximum aspiration vacuum attained to be any desirable level. It also allows the average pressure experienced by the eye to be lower in counter distinction to prior art surgery methods, where the average pressure was increased to help compensate for the flow surge. The only limit to the reduction of the average pressure is the pressure experienced when aspiration is flowing normally. This pressure needs to maintain the anterior chamber and allows space for surgery.

As will be appreciated by those skilled in the art, while the preferred embodiment device 10 is attached to the handpiece 11, improvement in surgical procedures can be obtained by mounting control device elsewhere with respect to the surgical machine 19.

Figure 7:
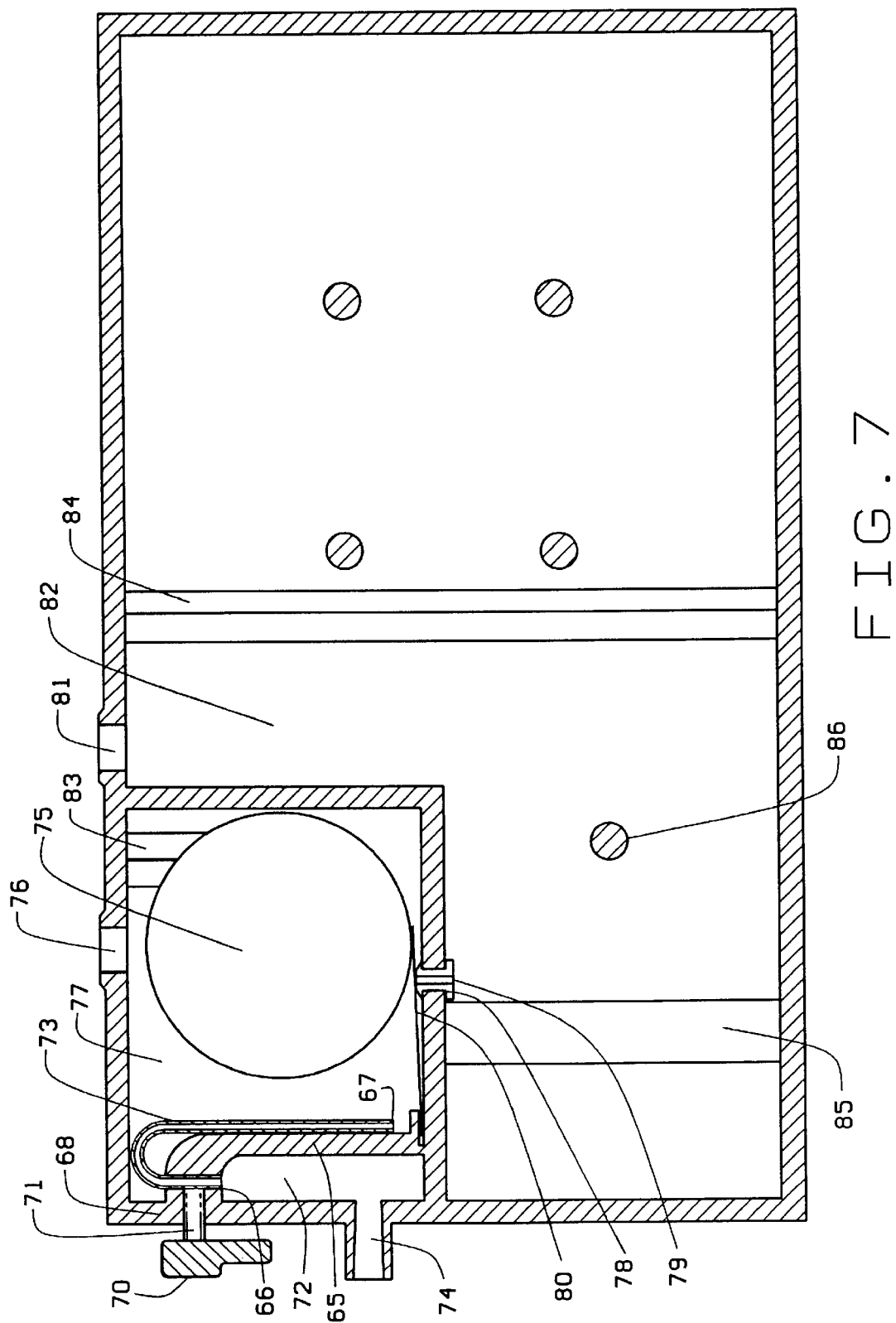
FIG. 7 is a diagrammatic view of a second illustrative embodiment of device of the present invention.

Merely by way of example, the second embodiment of my device may be incorporated in to collection cassettes of the type disclosed in U.S. Pat. Nos. 5,584,824 and/or 5,704,927, assigned to the Assignee of the present invention, the disclosures which are incorporated herein by reference. The cassette shown in FIG. 7 includes a first chamber 77 a second chamber 82. The chambers 77 and 82 have a float type valve 75 connecting the two chambers. The larger of the chambers, denominated by the reference numeral 82, is used as an accumulator for a high level of vacuum and for storage of aspirated material. The pressure in the smaller chamber 77 is controlled by an external mechanism, not shown, using the vacuum stored in the larger chamber 82. Ports 76 and 81 are provided for connection to the external vacuum control mechanism. The float type valve 75 is used to control the transfer material from the smaller chamber to the larger chamber. The valve includes a float 75 and an orifice 78. The orifice 78 has a through hole 79 formed in it, the opening of which is controlled by a flap 80. In this embodiment, a third chamber 72 is positioned upstream of the chamber 77. The chamber 72 has a connection port 74 associated with it, which is intended to receive aspirating tubing 26 in the manner described above. A tube 73, preferably constructed from a pliable material such as silicone or other suitable material, connects the chamber 72 to the chamber 77 through a wall 65. The tube 73 is arranged so that the first end 66 is at the top of the chamber 72, in reference to FIG. 7, while the second end 67 is positioned near the lower portion of the chamber 77, again reference to FIG. 7. An adjustment structure 71 controls the opening of the tube 73 by exerting a force against one side of the tube, thereby forming a variable orifice. The position of the adjustment structure 71 is controlled by a control knob 70. The adjustment structure 71 again may be threadedly engaged with a sidewall 68 of the cassette in a conventional manner. The device includes a pair of prism 83 and 84 respectively, which are provided to permit optical sensing of the fluid levels. A third prism 85 also is provided to permit illuminating the front of the cassette. A plurality of supports 86 also are provided to strengthen the walls of the chamber 82.

In this embodiment, as part of the surgery set up, a prime cycle is preformed to remove air from the aspiration path. During the prime cycle, the surgery machine applies a vacuum to port 76 of the aspiration cassette. The vacuum is transmitted through tube 73 to chamber 72. Connection 74 transmits the vacuum to the aspiration tubing 26, which in turn is connected to the handpiece 11. Fluid replaces the air inside the various tubes and connectors. Eventually, chamber 72 fills with aspiration fluid. All air will be removed from the chamber because of the location of the inlet end 66 of the tube 73. Fluid will exit tube 73 and begin to fill chamber 77. The outlet of tube 73 is placed lower than the fluid level necessary in chamber 77 to cause the float valve to transfer fluid to chamber 82. Because of the placement of the outlet end 67 of tube 73. After the prime cycle is preformed, the end 67 always remains in fluid within the chamber 77. In the event the fluid flows backward through tube 73, no air will enter the tube. Because both ends remain in liquid. Solids that enter chamber 72 through connection 74 will settle to the bottom of chamber of 72. In effect, the chamber 72 performs a filter function. The flow rates encountered in phacoemulsification surgery are not great enough to cause disturbance in chamber 72 during operation of the surgical instrument. After the aspiration path has had air removed, the desired flow is adjusted by turning the control knob 70. As before, the desired maximum attained vacuum is adjusted on the surgery machine 19. Again, the pitch of the adjustment 71 and the internal diameter of the tube 73 determined the flow adjustment range and sensitivity. Those skilled in the art will recognize that in this embodiment, it is preferred if aspiration tubing 26 is constructed so that it is able to resist diameter changes with pressure changes.

During surgery, the pressure at the ultrasound needle tip 13 are different from those experience with prior art methods employing a constant vacuum surgery machine for phacoemulsification surgery. When the ultrasound needles is not occluded, the variable orifice in the cassette is the greatest flow restriction in the aspiration flow path.

When the tip of the ultrasound needle becomes partially occluded, the vacuum level in the ultrasound needle will increase. When the tip of the ultrasound needle becomes fully occluded, the vacuum level in the ultrasound needle will equal the vacuum at the cassette. The maximum vacuum level attained when the needle is occluded is adjusted independently from flow rate attained when the needle is not occluded.

While this embodiment is an improvement over prior art devices, it is susceptible to post occlusion flow surges. Depending on the length of aspiration tubing used and the material form which the tubing is formed, the internal diameter of the tubing likely will change under vacuum. However, if relatively non-compliant tubing is employed, this embodiment will function well for its intended purpose, especially when compared to prior constant flow surgery machine operation.

Figure 8:
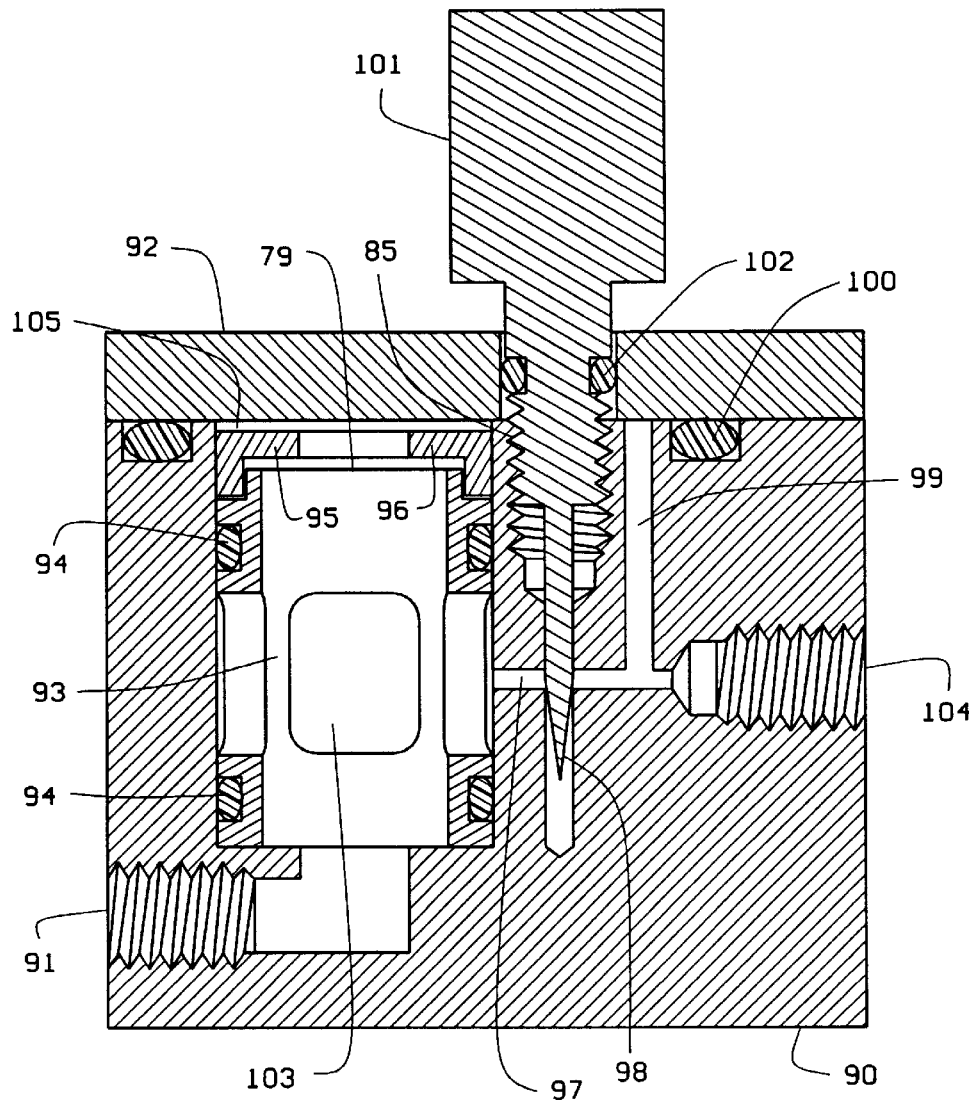
FIG. 8 is a diagrammatic view of a third illustrative embodiment of surge suppression device of the present invention.

Referring now to FIG. 8, a third embodiment of control device of the present invention is shown. This embodiment is designed to be used anywhere along the aspiration tubing 26, between the surgery machine 19 and the ultrasound handpiece 11, without actually being attached to the handpiece.

An enclosure 90 preferably is constructed from a material of sufficient strength, like polycarbonate plastic, which allows one to see the interior of the structure. It may also be constructed from other like and unlike materials, including stainless steel or titanium, in cases where the device is intended to be resusable. In any event, a fluid inlet 91 and an outlet 104 are provided in the enclosure 90. The inlet and outlet include suitable conventional structure permitting attachment of the device in the aspiration line of the surgical machine 19. A fluid flow path extends from the inlet 91 to the outlet 104. The fluid flow path includes a channel 97 of reduced internal diameter when compared to the inlet and outlet portions of the device. A cylindrical filter frame 93 is position downstream of the inlet 91 and upstream of the channel 97. The filter frame 93 has a plurality of windows 103 formed in it. The axial inner wall of the filter frame 93 is lined with hydrophilic material, which again is preferably constructed from a fine mesh material such as a polyester cloth with a mesh opening between 20 and 200 microns. As indicated above, other materials and/or opening sizes may be employed, if desired. Once the filter material is wetted, only liquid will pass through the hydrophilic filter. Fluid entering the device must go inside the frame 93, through the hydrophilic filter, then through the windows 103 of the filter portion of the frame 93 to the channel 97.

An adjustment means 101 includes a tapered tip 98, which is movable within the channel 97 along threads 85. When the tip 98 is in its closed position, as shown in FIG. 8, it completely occludes channel 97. As the tip 98 is moved upwardly, upward being reference to FIG. 8, the liquid flow restriction in the channel 97 is reduced.

A filter cap 96 closes one end of the filter frame 93. A clear space 95 is formed between the upper end 79 of the filter frame 93 and the cap 96. The space 95 contains a hydrophobic membrane that preferably is constructed from Teflon or other similar material that exhibits hydrophobic characteristics. The hydrophobic membrane allows air, but not liquid, to pass to a space 105. The space 105 is formed between the cap 96 and a cover 92 of the device. The space 105 in turn is in fluid connection with an opening 95. The opening 95 is in fluid communication with channel 97, which is positioned on the downstream side of the adjustment device 101. Again, in this embodiment, any air bubbles that enter the device 10 will float to the hydrophobic membrane where the bubbles will be allowed to pass to the fluid outlet 104, regardless of the adjustment position of the tapered tip 98.

In operation, as with the embodiment described above, a prime cycle is preformed to clear air from the aspiration path. Maximum vacuum is set on the surgery machine 19. On a constant flow surgery machine, the flow rate is adjusted higher than the desired amount of flow during surgery. The adjustment 101 is positioned to give the desired amount of flow when the ultrasound needle is not occluded. In general, I prefer to locate the device in the aspiration tubing 26 as close as practical to the ultrasound handpiece. Again, the length of tubing between the device inlet 91 and the ultrasound handpiece 11 can cause some post occlusion flow surge, because of the change in the internal diameter of the tubing. However, if relatively non-compliant tubing is used, this embodiment performs in a manner similar to that disclosed conjunction with FIG. 2.

The embodiment of FIG. 8 offers the advantage of being relatively easy to manufacture as a reusable device with a disposable filter element. It also is readily applicable to an automated drive for flow adjustment.

Numerous variations, within the scope of the appended claims will be apparent to those skilled in the art in light of the foregoing description and accompanying drawings. Merely by way of example while various materials were described as preferred, other materials are compatible with the broader aspects of the invention. For the purpose of this specification, "non-compliant" tubing means tubing which maintains a relatively constant internal diameter under the vacuum encountered in phacoemulsification eye surgery. The various devices described may be constructed in either reusable or disposable embodiments without departing from the scope of the appended claims.

What is claimed is:

1. A device for use in eye surgery comprising:
    an enclosure having an inlet and outlet, said enclosure defining a fluid flow passage therebetween, said flow including a liquid component and a gas component;
    a filter assembly mounted in said flow passage, said filter permitting passage of said fluid but preventing passage of solid material;
    a valve restriction mounted in said flow passage, downstream of said filter; and
    an adjustment structure for varying the size of the restriction operatively associated with valve restriction so as to enable a user to maintain stable fluid pressure in the eye.

2. The device of claim 1 further including a handpiece, the enclosure including a portion adapted for connection to the handpiece.

3. The device of claim 1 further including a cassette storage assembly, the eye surgery device being mounted within said cassette storage assembly.

4. The device of claim 2 including an aspirating line between said device and said handpiece, said device being mounted in said aspirating line.

5. The device of claim 4 wherein said valve is adjustable.

6. The device of claim 5 wherein said valve is a needle valve.

7. The device of claim 5 wherein said valve includes a deformable structure.

8. An anti-cornea collapsing device for use in performing phacoevacuation comprising:
    an enclosure, said enclosure having an inlet side for receiving aspirating material including fluid and solids from the eye, and an outlet side, said enclosure defining a first passage between the inlet and outlet;
    a valve positioned in said passage for restricting suction through said device; and
    a filter mounted upstream of said passage, said filter permitting passage of fluid in at least one operating condition of said device, while generally inhibiting flow of solids through said device, said filter including a labyrinth structure.

9. The device of claim 8 further including a second flow passage between said filter and the outlet of said device.

10. The device of claim 9 wherein said valve is a needle valve.

11. The device of claim 8 further including an attachment device for attaching said device to an ultrasound handpiece.

12. An anti-cornea collapsing device for use in performing eye surgery comprising:
    an enclosure defining an inlet and outlet, and a flow passage therebetween;
    a restriction formed in said flow passage;
    a filter in said flow passage upstream of said restriction, said filter permitting passage of fluid but inhibiting passage of solid material;
    said enclosure defining storage area upstream of said filter; and
    a hand piece for performing eye surgery, said enclosure being removeably mounted to said handpiece.

13. The device of claim 12 wherein the device is disposable.

14. The device of claim 13 wherein restriction is adjustable.

15. The device of claim 14 further including a pair of filters operatively positioned in series with one another.

16. The device of claim 15 wherein said enclosure defines an air path extending from at least one filter to the downstream side of said restriction.

17. A device for performing eye surgery comprising:

an enclosure having an inlet and an outlet, said enclosure defining a fluid flow passage there between, said fluid flow including a liquid component and a gas component;

a filter assembly mounted in said fluid flow passage, said filter assembly permitting passage of said fluid but preventing passage of solid material;

a valve restriction mounted in said flow passage downstream of said filter; and an adjustment structure for varying the size of the restriction operatively associated with the restriction so as to enable a user to maintain stable fluid pressure in the eye.

18. The device of claim 17 further including a handpiece, the enclosure including a portion adapted for connection to the handpiece.

19. The device of claim 17 wherein said valve is adjustable.

20. The device of claim 17 where said valve is a needle valve.

21. The device of claim 17 wherein the valve is a deformable structure.

* * * * *